(12) United States Patent
Stern et al.

(10) Patent No.: US 8,821,431 B2
(45) Date of Patent: Sep. 2, 2014

(54) AIR GAP FOR SUPPORTING CELLS

(75) Inventors: Yaki Stern, Shoham (IL); Yoram Rozy, Caesarea (IL)

(73) Assignee: Beta O2 Technologies Ltd., Petach-Tikva (IL)

( * ) Notice: Subject to any disclaimer, the term of this patent is extended or adjusted under 35 U.S.C. 154(b) by 1051 days.

(21) Appl. No.: 12/676,744

(22) PCT Filed: Sep. 7, 2008

(86) PCT No.: PCT/IL2008/001204
§ 371 (c)(1), (2), (4) Date: Aug. 13, 2010

(87) PCT Pub. No.: WO2009/031154
PCT Pub. Date: Mar. 12, 2009

(65) Prior Publication Data
US 2010/0312165 A1    Dec. 9, 2010

Related U.S. Application Data

(60) Provisional application No. 60/993,052, filed on Sep. 7, 2007.

(51) Int. Cl.
*A61M 37/00* (2006.01)
*C12M 1/00* (2006.01)
*C12M 1/04* (2006.01)
*C12M 1/12* (2006.01)

(52) U.S. Cl.
CPC .............. *C12M 31/10* (2013.01); *C12M 21/02* (2013.01); *C12M 23/24* (2013.01); *C12M 25/06* (2013.01)
USPC ........................ 604/19; 604/891.1; 435/292.1

(58) Field of Classification Search
CPC ................................ A61M 37/00; C12M 1/00
USPC ................ 604/6.14, 6.16, 19, 23, 93.01, 175, 604/288.01–288.04, 500–502, 604/890.1–891.1; 424/93.1–93.7, 195.17, 424/422–425; 435/41, 69.4, 289.1, 292.1, 435/293.1–293.2; 210/321.75–321.87, 210/323.1, 649
See application file for complete search history.

(56) References Cited

U.S. PATENT DOCUMENTS 2,564,977 A    8/1951    Hu
4,352,883 A    10/1982   Lim
(Continued)

FOREIGN PATENT DOCUMENTS

GB    2024012    1/1980
JP    06-507412    8/1994
(Continued)

OTHER PUBLICATIONS

Stagner, et al., "The pancreas as an islet transplantation site", Sep. 1, 2007, Journal of the Pancreas, vol. 8, No. 5, pp. 628-636.
(Continued)

*Primary Examiner* — David Isabella
*Assistant Examiner* — Yashita Sharma
(74) *Attorney, Agent, or Firm* — Sughrue Mion, PLLC

(57) ABSTRACT

Apparatus is provided including a housing, configured for insertion into a body of a subject, one or more oxygen reservoirs disposed within the housing, at least one layer of functional cells, disposed within the housing, and gaseous oxygen disposed within the one or more oxygen reservoirs. The apparatus is arranged to permit passage of the gaseous oxygen from the one or more oxygen reservoirs to the functional cells. The one or more oxygen reservoirs define first and second air gaps, the first air gap is configured to receive oxygen in a first concentration, and the second air gap is disposed adjacent to the layer of functional cells and stores the oxygen in a second concentration that is lower than the first concentration. Other applications are also described.

9 Claims, 7 Drawing Sheets

(56) References Cited

U.S. PATENT DOCUMENTS

| | | |
|---|---|---|
| 4,402,694 A | 9/1983 | Ash et al. |
| 4,631,053 A | 12/1986 | Taheri et al. |
| 4,721,677 A | 1/1988 | Clark, Jr. |
| 4,801,291 A | 1/1989 | Loori |
| 5,011,472 A | 4/1991 | Aebischer et al. |
| 5,029,579 A | 7/1991 | Trammell |
| 5,101,814 A | 4/1992 | Palti |
| 5,116,494 A | 5/1992 | Chick et al. |
| 5,262,055 A | 11/1993 | Bae et al. |
| 5,336,209 A | 8/1994 | Porzilli |
| 5,381,075 A | 1/1995 | Jordan |
| 5,407,685 A | 4/1995 | Malchesky et al. |
| 5,427,935 A | 6/1995 | Wang et al. |
| 5,443,508 A | 8/1995 | Giampapa |
| 5,529,066 A | 6/1996 | Palti |
| 5,578,022 A | 11/1996 | Scherson et al. |
| 5,578,314 A | 11/1996 | Cochrum et al. |
| 5,614,378 A | 3/1997 | Yang et al. |
| 5,662,625 A | 9/1997 | Westwood |
| 5,702,444 A | 12/1997 | Struthers et al. |
| 5,713,888 A | 2/1998 | Neuenfeldt et al. |
| 5,741,334 A | 4/1998 | Mullon et al. |
| 5,788,682 A | 8/1998 | Maget |
| 5,792,090 A | 8/1998 | Ladin |
| 5,834,005 A | 11/1998 | Usala |
| 5,855,070 A | 1/1999 | Grabowski |
| 5,855,613 A | 1/1999 | Antanavich et al. |
| 5,879,709 A | 3/1999 | Soon-Shoing et al. |
| 5,902,745 A | 5/1999 | Butler et al. |
| 5,912,005 A | 6/1999 | Lanza et al. |
| 6,000,403 A | 12/1999 | Cantwell |
| 6,091,974 A | 7/2000 | Palti |
| 6,148,232 A | 11/2000 | Avrahami |
| 6,179,804 B1 | 1/2001 | Satterfield |
| 6,268,161 B1 | 7/2001 | Han et al. |
| 6,368,592 B1 | 4/2002 | Colton et al. |
| 6,372,244 B1 | 4/2002 | Antanavich et al. |
| 6,383,478 B1 | 5/2002 | Prokop et al. |
| 6,630,154 B1 | 10/2003 | Fraker et al. |
| 6,649,384 B2 | 11/2003 | Walsh et al. |
| 6,767,342 B1 | 7/2004 | Cantwell |
| 6,815,186 B2 | 11/2004 | Clark, Jr. et al. |
| 6,821,107 B1 | 11/2004 | Hara |
| 6,960,351 B2 | 11/2005 | Dionne et al. |
| 7,892,222 B2 | 2/2011 | Vardi et al. |
| 8,012,500 B2 | 9/2011 | Rotem et al. |
| 8,043,271 B2 | 10/2011 | Stern et al. |
| 2002/0022016 A1 | 2/2002 | Walsh et al. |
| 2003/0050622 A1 | 3/2003 | Humes et al. |
| 2003/0087427 A1 | 5/2003 | Colton et al. |
| 2003/0113302 A1 | 6/2003 | Revazova et al. |
| 2004/0109302 A1 | 6/2004 | Yoneda et al. |
| 2004/0133188 A1 | 7/2004 | Vardi et al. |
| 2004/0178358 A1 | 9/2004 | Kreiss et al. |
| 2005/0025680 A1 | 2/2005 | Monzyk et al. |
| 2005/0136092 A1 | 6/2005 | Rotem et al. |
| 2006/0024276 A1 | 2/2006 | Ricordi |
| 2006/0035370 A1 | 2/2006 | Lee et al. |
| 2006/0063140 A1 | 3/2006 | Nussinovitch et al. |
| 2007/0190038 A1 | 8/2007 | Suzuki |
| 2008/0086042 A1 | 4/2008 | Brister et al. |
| 2009/0012502 A1 | 1/2009 | Rotem et al. |

FOREIGN PATENT DOCUMENTS

| | | |
|---|---|---|
| JP | 08-512282 | 12/1996 |
| WO | WO 90/15526 | 12/1990 |
| WO | 92/19195 A1 | 11/1992 |
| WO | 94/20076 A1 | 9/1994 |
| WO | WO 00/78920 | 12/2000 |
| WO | WO 01/50983 | 7/2001 |
| WO | WO 03/011445 | 2/2003 |
| WO | WO 2006/059322 | 6/2006 |
| WO | WO 07/138590 | 3/2007 |
| WO | 2008/065660 A2 | 6/2008 |
| WO | 2008/079997 A2 | 7/2008 |
| WO | 2008/112190 A1 | 9/2008 |
| WO | WO 2009/031154 | 3/2009 |
| WO | 2010/032242 A1 | 3/2010 |

OTHER PUBLICATIONS

An International Search Report and a Written Opinion, both dated Jan. 25, 2010, which issued during the prosecution of Applicant's PCT/IL09/00905.
Office Action dated May 14, 2010, which issued during prosecution of Applicant's U.S. Appl. No. 12/315,102.
Office Action dated Jun. 22, 2010, which issued during the prosecution of Applicant's U.S. Appl. No. 10/466,069.
International Search Report and Written Opinion, both dated Jun. 9, 2010, issued during the prosecution of Applicant's PCT/IL09/01114.
An office Action dated May 31, 2011, which issued during the prosecution of Applicant's Japanese Patent Application No. 2007-544006.
An International Preliminary Report on Patentability, dated May 31, 2011, which issued during the prosecution of Applicant's PCT/IL2009/001114.
An English Translation of an Office Action dated Aug. 26, 2013 which issued during the prosecution of Chinese Patent Application No. 200980155498.6.
An Office Action dated Sep. 16, 2013 which issued during the prosecution of Australian Patent Application No. 2009321193.
Wu H et al., "In-situ electrochemical oxygen generation with an immunoisolation device", Ann N Y Acad Sci 875:105-25 (1999).
L. Leheninger, Biochemistry, Worth Publishers, Inc. 1978, Chapter 14, pp. 363-364.
Smith AJ, "Acetate assimilation by nitrobacter agilis in relation to its 'obligate autotrophy'", Journal of Bacteriology 95:844 (1968).
Klueth, et al., "Enhancement of implantable glucose sensor function in vivo using gene transfer-induced neovascularization", Biomaterials, vol. 26, No. 10, Apr. 2005. (an abstract).
Silva AI et al., "An overview on the development of a bio-artificial pancreas as a treatment of insulin-dependent diabetes mellitus," Med Res Rev 26 (2) : 181-222 (2006).
Faithful, N. S. Anaesthesia, 42, pp. 234-242 (1987).
Lacy PE et al., "Maintenance of normoglycemia in diabetic mice by subcutaneous xenografts of encapsulated islets," Science 1782-4 (1991).
Kaisers U et al., "Liquid ventilation," British Journal of Anaesthesia 91(1) : 143-151 (2003).
Lorch H et al., "Central venous access ports placed by interventional radiologists: experience with 125 consecutive patients", Journal CardioVascular and interventional radiology, pp. 180-184, Issue vol. 24, No. 3 (2001).
An International Search Report dated Feb. 5, 2009, which issued during the prosecution of Applicant's PCT/IL08/01204.
Waschke KF, et al., "Modified haemolglobins and perfluorocarbons" (Current opinion in Anaesthesiology. 12(2): 195-202 (1999).
An office Action dated Jan. 7, 2011, which issued during the prosecution of Applicant's U.S. Appl. No. 11/001,556.
An Interview Summary dated Feb. 28, 2011, which issued during the prosecution of Applicant's U.S. Appl. No. 11/001,556.
Francis-Floyd, Ruth; Dissolved Oxygen for Fish Production; Feb. 2003.
An Office Action dated Sep. 8, 2010, which issued during the prosecution of U.S. Appl. No. 12/315,102.
An Office Action dated May 14, 2010, which issued during the prosecution of U.S. Appl. No. 12/315,102.
Notice of Allowance dated Jul. 11, 2011, which issued during the prosecution of U.S. Appl. No. 12/315,102.
A Restriction Requirement dated Feb. 4, 2010, which issued during the prosecution of U.S. Appl. No. 12/315,102.
An Office Action dated Dec. 17, 2013, which issued during the prosecution of Canadian Patent Application No. 2,671,094.
An English Translation of an Office Action dated Dec. 8, 2011, which issued during the prosecution of Chinese Patent Application No. CN 200580047325.4.

(56) References Cited

OTHER PUBLICATIONS

An International Search Report dated Jan. 25, 2012, which issued during the prosecution of Applicant's PCT/IL11/00445.
An Office Action dated Mar. 2, 2012 which issued during the prosecution of Japanese Patent Application No. JP 2007-544006.
An Office Action dated May 14, 2012 which issued during the prosecution of U.S. Appl. No. 12/515,818.
An Office Action dated Apr. 24, 2012 which issued during the prosecution of U.S. Appl. No. 12/064,946.
An English Translation of an Office Action dated May 23, 2011 which issued during the prosecution of Japanese Patent Application No. JP 2007-544006.
An Office Action dated Mar. 13, 2014, which issued during the prosecution of U.S. Appl. No. 13/153,721.
Supplementry Europan Search Report dated Apr. 22, 2014 which issued during the prosecution of Applicant's European App No. 09 82 8728.

000# AIR GAP FOR SUPPORTING CELLS

CROSS-REFERENCE TO RELATED APPLICATIONS

This application is a U.S. national phase of PCT Application no. PCT/IL2008/001204 to Stern and Rozy, filed Sep. 7, 2008, which claims priority from U.S. Provisional Patent Application 60/993,052 to Rozy and Stern, entitled, "Air gap for supporting cells," filed on Sep. 7, 2007, which is incorporated herein by reference.

FIELD OF THE INVENTION

The present invention relates generally to implantable medical devices. Specifically, the present invention relates to an implantable device to generate and provide oxygen to transplanted cells, e.g., cells in transplanted pancreatic islets.

BACKGROUND OF THE INVENTION

Oxygen is essential to many physiological and metabolic processes, including aerobic metabolism. A lack of oxygen for implanted cells often leads to cell injury or death. Oxygen provision is a vital component in sustaining transplanted cells.

The success of many transplants is compromised not only due to graft-host rejections, but also on account of ischemic conditions generated by insufficient oxygen supply to the transplant. Following implantation of the cells, oxygen is provided to the implanted cells from the body tissue (mainly via diffusion). However, the natural diffusion rate is too low in order to provide the cells with a significant, necessary amount of oxygen.

In healthy individuals, insulin release is regulated so as to maintain blood glucose levels in the range of about 70 to 110 milligrams per deciliter. In diabetics, insulin is either not produced at all (Type I diabetes), or the body cells do not properly respond to the insulin that is produced (Type II diabetes). The result is elevated blood glucose levels.

PCT Publication WO 01/50983 to Vardi et al., and U.S. patent application Ser. No. 10/466,069 in the national phase thereof, which are assigned to the assignee of the present application and are incorporated herein by reference, describe an implantable device comprising a chamber for holding functional cells and an oxygen generator for providing oxygen to the functional cells. In one embodiment, the oxygen generator is described as comprising photosynthetic cells that convert carbon dioxide to oxygen when illuminated. In another embodiment, the oxygen generator is described as comprising electrodes that produce oxygen by electrolysis.

US Patent Application Publication 2005/0136092 to Rotem, which is incorporated herein by reference, describes apparatus including a chamber, which is adapted to be implanted in a body of an individual, the chamber including functional cells and chlorophyll-containing elements comprising chlorophyll of an obligate photoautotroph. Typically, the chlorophyll-containing elements include intact photosynthetic cells and/or isolated chloroplasts. The chlorophyll-containing elements provide oxygen to the functional cells and/or consume carbon dioxide produced by the functional cells. The chamber has one or more walls that are adapted to be permeable to nutrients and substances produced or secreted by the cells. The walls also typically immunoisolate the cells from constituents of the body. The chamber is adapted to be implanted under skin of the subject, or in the peritoneum. The apparatus further comprises a light source that is adapted to provide light to the chlorophyll-containing elements. The chamber may comprise an oxygen sensor that detects an oxygen concentration in a vicinity of the functional cells, and/or in a vicinity of the chlorophyll-containing elements. Providing the light in the series of pulses generally reduces power consumption of the apparatus, and/or provides control of the quantity of oxygen produced by the chlorophyll-containing elements, and/or provides control of the quantity of carbon dioxide consumed by the chlorophyll-containing elements. In some embodiments of the invention, the chamber comprises an oxygen reservoir, which typically comprises a material that stores and releases oxygen, such as responsively to an oxygen concentration in a vicinity of the reservoir. The oxygen reservoir typically stores oxygen produced by the chlorophyll-containing elements that is in excess of the current needs of the functional cells, and releases the stored oxygen if insufficient oxygen is later generated by the chlorophyll-containing elements.

U.S. Pat. No. 6,368,592 to Colton et al., which is incorporated herein by reference, describes techniques for supplying oxygen to cells in vitro or in vivo by generating oxygen with an oxygen generator that electrolyzes water to oxygen and hydrogen. The oxygen generator is described as supplying oxygen to cells contained in an encapsulating chamber for implanting in the body, such as an immunoisolation chamber bounded by a semipermeable barrier layer that allows selected components to enter and leave the chamber. A bioactive molecule may be present with the cells.

U.S. Pat. No. 4,721,677 to Clark, Jr. et al., which is incorporated herein by reference, describes an implantable biosensor and method for sensing products, such as hydrogen peroxide, generated from an enzymatic reaction between an analyte, like glucose, and an enzyme in the presence of oxygen. The biosensor is described as being equipped with an enclosed chamber for containing oxygen, and can be adapted for extracting oxygen from animal tissue adjacent the container. The biosensor is designed to optically or electrically sense products generated from the enzymatic reaction, which serve as a function of the analyte.

U.S. Pat. No. 6,960,351 to Dionne et al., which is incorporated herein by reference, describes an immunoisolatory vehicle for the implantation into an individual of cells which produce a needed product or provide a needed metabolic function. The vehicle is comprised of a core region containing isolated cells and materials sufficient to maintain the cells, and a permselective, biocompatible, peripheral region free of the isolated cells, which immunoisolates the core yet provides for the delivery of the secreted product or metabolic function to the individual. The vehicle is described as being particularly well-suited to delivery of insulin from immunoisolated islets of Langerhans, and as being used advantageously for delivery of high molecular weight products, such as products larger than IgG. A method of making a biocompatible, immunoisolatory implantable vehicle is also described, consisting in a first embodiment of a coextrusion process, and in a second embodiment of a stepwise process. A method is described for isolating cells within a biocompatible, immunoisolatory implantable vehicle, which protects the isolated cells from attack by the immune system of an individual in whom the vehicle is implanted. A method is described of providing a needed biological product or metabolic function to an individual, comprising implanting into the individual an immunoisolatory vehicle containing isolated cells which produce the product or provide the metabolic function.

The '351 patent describes a vehicle that provides, in at least one dimension, sufficiently close proximity of any isolated cells in the core to the surrounding tissues of the recipient, including the recipient's bloodstream, in order to maintain the viability and function of the isolated cells. However, the diffusional limitations of the materials used to form the vehicle do not in all cases solely prescribe its configurational limits. Certain additives can be used which alter or enhance the diffusional properties, or nutrient or oxygen transport properties, of the basic vehicle. For example, the internal medium can be supplemented with oxygen-saturated perfluorocarbons, thus reducing the needs for immediate contact with blood-borne oxygen. This is described as allowing isolated cells or tissues to remain viable while, for instance, a gradient of angiotensin is released from the vehicle into the surrounding tissues, stimulating ingrowth of capillaries.

References and methods for use of perfluorocarbons are described in Faithful, N. S. Anaesthesia, 42, pp. 234-242 (1987) and NASA Tech Briefs MSC-21480, U.S. Govt. Printing Office, Washington, D.C. 20402, which are incorporated herein by reference.

US Patent Application Publication 2005/0025680 to Monzyk et al., which is incorporated herein by reference, describes a photolytic cell and a photolytic artificial lung incorporating such a cell. The photolytic artificial lung converts water to oxygen for blood absorption, regulates pH, removes carbon dioxide, and co-produces electrical power. The photolytic artificial lung includes a photolytic cell where all of the chemical reactions occur. Additionally, Monzyk describes photolytically-sensitive materials for oxygen generation. These materials are useful for gas-free artificial lung fabrication. The photolytic cell is described as being useful for directing chemical reactions in organs other than the lung, and for maintaining breathing air in confined systems.

The following patents and patent applications, which are incorporated herein by reference, may be of interest:
U.S. Pat. No. 6,268,161 to Han, et al.
US Patent Application Publication 2006/0024276 to Ricordi, et al.
U.S. Pat. No. 6,815,186 to Clark, Jr. et al.
U.S. Pat. No. 6,630,154 to Fraker, et al.
US Patent Application Publication 2003/0113302 to Revazova, et al.
U.S. Pat. No. 6,383,478 to Prokop, et al.

The following articles, which are incorporated herein by reference, may be of interest:
Lacy P E et al., "Maintenance of normoglycemia in diabetic mice by subcutaneous xenografts of encapsulated islets," Science 1782-4 (1991)
Silva A I et al., "An overview on the development of a bio-artificial pancreas as a treatment of insulin-dependent diabetes mellitus," Med Res Rev 26(2):181-222 (2006)
Kaisers U et al., "Liquid ventilation," British Journal of Anaesthesia 91(1):143-151 (2003)

SUMMARY OF THE INVENTION

In some embodiments of the present invention, apparatus for containing transplanted cells comprises a housing that is designated for implantation into the body of a subject. The transplanted cells typically comprise functional cells, e.g., pancreatic islet of Langerhans cells. At least one layer of functional cells, as well as an oxygen generator comprising at least one photosynthetic oxygen supply are disposed within the housing. Typically, the functional cells are disposed in a layer of liquid or gel, such as alginate, agarose, or polyethylene glycol (PEG) and/or dispersed in a three-dimensional biodegradable or non-biodegradable fibrillar matrix. The oxygen generator is typically coupled to a support that is disposed within the housing.

The housing comprises air gaps, e.g., an area of gas comprising oxygen and carbon dioxide, disposed in part between the layers of the system. In some embodiments, the apparatus comprises one or a plurality of photosynthetic oxygen supplies, e.g., between two and four oxygen supplies, typically two oxygen supplies.

Typically, each photosynthetic oxygen supply comprises at least one light source and at least one, e.g., a pair, of layers of a photosynthetic source, e.g., algae. Typically, for embodiments in which a pair of layers of algae is used, the light source is disposed between first and second layers of the pair of algae layers.

The plurality of photosynthetic oxygen supplies are disposed as layers with respect to the support. Typically, the layers of algae in each oxygen supply provide a large surface area in which a ratio of the surface area of the algae to the surface area of the functional cells is greater than 1:1. An air gap is provided between each layer of photosynthetic oxygen supplies, and functions as a conduit for oxygen diffusion as well as a reservoir for storing excess oxygen produced by the oxygen generator. It is hypothesized by the inventors that an air gap is capable of storing at least four orders of magnitude more oxygen molecules relative to the oxygen-storage capacity of a liquid chamber.

The air gaps typically increase the diffusivity of the oxygen passing from the oxygen supply to the functional cells.

The photosynthetic oxygen supply typically comprises a light source and at least one layer of algae disposed upon an agarose matrix. Typically, the photosynthetic oxygen supply comprises a first and a second layer of algae, and the light source is disposed therebetween. It is to be noted that up to 12 layers of algae may be disposed on either side of the light source. In some embodiments, at least one of the layers of algae physically contacts the light source. Such configuration increases the surface area of the algae, allowing more light to contact the algae, and effectively facilitates increased oxygen production thereby. The photosynthetic oxygen supply is typically disposed between first and second layers of functional cells and is partitioned therefrom by respective first and second gas-permeable membranes. The first and second layers of functional cells are typically but not necessarily disposed at opposite ends of the housing. The gas within the housing is disposed at least in part in an air gap between the first layer of functional cells and the first layer of algae and in an air gap between the second layer of functional cells and the second layer of algae.

In some embodiments, a plurality of photosynthetic oxygen supplies are disposed within the housing. The oxygen supplies are typically arranged in layers between the first and second layers of functional cells. Each oxygen supply is separated from the next oxygen supply by an air gap. For embodiments in which the oxygen supply comprises first and second layers of algae, each layer of algae is in contact with the gas in a respective air gap adjacent thereto.

Typically, the air gaps are configured to store and provide a buffer for the oxygen generated by the layers of algae. Typically, the algae produce oxygen at a generally constant rate while the functional cells consume oxygen at a variable rate. For embodiments in which the functional cells comprise islets of Langerhans, upon sensing a need for insulin, the functional cells consume oxygen at a higher rate during the production of insulin than at rest. Thus, the reservoirs provided by the air gap store the excess oxygen produced by the oxygen generator in order to meet the variable demand of the functional cells. Alternatively or additionally, the air gaps permit diffusion of the oxygen from the oxygen supplies to the functional cells. In such embodiments, the housing typically comprises a channel in communication with the air gaps which is configured to collect oxygen from the air gaps and to channel the oxygen toward the gas permeable membrane where it is ultimately diffused to the functional cells.

Typically, the oxygen generator is configured to supply oxygen to the functional cells and to sustain the functional cells for a period preceding vascularization around the housing, e.g., at least several weeks or months. During the period in which the oxygen generator supplies oxygen to the cells, the cells typically secrete factors that induce vascularization in fibrotic tissue surrounding the housing. Once the fibrotic tissue has become vascularized, the transplanted cells generally survive due to oxygen transfer from the newly-vascularized tissue, even in the absence of oxygen produced by the oxygen generator.

The use of a photosynthesizing system such as photosynthesizing algae and a light source is described in PCT Publication WO 01/50983 to Vardi et al., or US Patent Application Publication 2005/0136092 to Rotem, which are incorporated herein by reference.

In some embodiments, the support comprises a scaffold that houses the algae upon an agarose matrix.

In some embodiments, each layer of algae is disposed within a gas-permeable membrane and the membrane-enclosed algae are disposed adjacently to the light source.

For some applications, the membrane is coupled to the support in a manner in which an air gap is disposed between the layer of algae and the light source. In such an embodiment, a first air gap is provided adjacent to the light-remote surface of the algae (i.e., between the surface of the algae disposed remotely with respect to the light source and the light-remote surface of a neighboring layer of algae), and a second air gap is provided adjacent to the light-adjacent surface of the algae (i.e., between light source and the surface of the algae disposed adjacent to the light source). The first and second air gaps allow the oxygen to diffuse into the housing through both surfaces of the layer (i.e., the light-remote surface and the light-adjacent surfaces of the layer), thereby increasing the diffusion rate of the oxygen from the algae layer. The algae produce most of the oxygen in the vicinity of the layer that is closest to the light source (i.e., the light-adjacent surface). The oxygen from the vicinity is allowed to diffuse into the air gap via the light-adjacent surface without having to diffuse through the algae layer first before exiting toward the air gap via the light-remote surface.

For embodiments in which at least two photosynthetic oxygen supplies are disposed within the support, the layers of algae in each oxygen supply are relatively thin and have a width of between 150 um and 500 um, typically, about 200 um. The width of the algae layer allows for: (a) light to pass through the algae layer from the first oxygen supply, across an air gap and to the algae layer of the neighboring second oxygen supply, and (b) enhanced diffusion of the oxygen from the algae disposed adjacent to the light source, through the algae layer, and finally to the air gaps. The width of the algae layers reduces the time needed for oxygen transport through the algae layers, thereby facilitating increased diffusion of the oxygen through the layer and toward the air gaps. This increased diffusion enables the device to more rapidly supply sufficient oxygen to meet the oxygen consumption rate of the functional cells. Additionally, this diffusion of oxygen away from the algae disposed adjacently to the light source helps reduce the threat of oxygen toxicity for the algae disposed adjacently to the light source.

For applications in which the functional cells are islets of Langerhans, the oxygen supply typically supplies oxygen to the islets at a rate of between about 4 and 40 micromoles/hour per 100,000 transplanted islets, or as otherwise appropriate based on the type and number of functional cells and/or the body weight of the subject.

There is therefore provided, in accordance with an embodiment of the present invention, apparatus, including:

a housing, configured for insertion into a body of a subject;

one or more photosynthetic oxygen supplies, disposed within the housing;

at least one layer of functional cells, disposed within the housing, and configured to receive oxygen from the one or more oxygen supplies; and a gas disposed to permit passage therethrough of the oxygen from the one or more oxygen supplies to the cells, the gas disposed at least in part between the layer of functional cells and at least one of the oxygen supplies.

In an embodiment, the functional cells include pancreatic islet cells.

In an embodiment, the gas includes oxygen and carbon dioxide.

In an embodiment, the housing includes a semi-permeable membrane having associated therewith a molecular weight cutoff, the membrane being disposed with respect to the functional cells so as to protect the functional cells from components of a body fluid of the subject having molecular weights higher than the cutoff.

In an embodiment, the membrane includes a gas-permeable membrane.

In an embodiment, each photosynthetic oxygen supply includes:

a light source; and at least one first layer of algae, positioned to receive light from the light source.

In an embodiment, the apparatus includes a membrane disposed between the oxygen supply and the functional cells, the membrane having associated therewith a molecular weight cutoff configured to restrict passage of algae therethrough.

In an embodiment, the light source has an input electrical power between 5 mW/(cm^2 of algae) and 50 mW/(cm^2 of algae).

In an embodiment, an energy of illumination applied to the algae by the light source is at a rate of between 0.2 mW/(cm^2 of algae) and 2.0 mW/(cm^2 of algae).

In an embodiment, the first layer of algae has a width of between 100 um and 2000 um.

In an embodiment, the first layer of algae has a width of between 100 um and 300 um.

In an embodiment, the at least one layer of algae is in contact with the gas.

In an embodiment, the gas is disposed in part between the layer of algae and the light source.

In an embodiment, the at least one layer of algae includes a first and a second layer of algae, and the light source is disposed between the first and second layers.

In an embodiment, both the first and second layers of algae are in contact with the gas.

In an embodiment, the one or more layers of functional cells include a first and a second layer of functional cells, and the first and second layers of functional cells are in communication with the first and second layers of algae.

In an embodiment, the first layer of functional cells is spaced apart from the first layer of algae by a distance of between 1000 um and 6000 um.

In an embodiment, the first layer of functional cells is spaced apart from the first layer of algae by a distance of between 100 um and 500 um.

In an embodiment, the gas is disposed at least in part between the first layer of algae and the first layer of functional cells, and between the second layer of algae and the second layer of functional cells.

In an embodiment, the first layer of functional cells is spaced apart from the first layer of algae by a distance of between 1 um and 1000 um.

In an embodiment, the light source includes a first light source configured to be in optical communication with at least a first surface of the first layer of algae, and the apparatus further includes a second light source configured to be in optical communication with at least the first surface of the first layer of algae, the first layer of algae being disposed between the first and second light sources.

In an embodiment:

the apparatus includes a second layer of algae, the second layer of algae being in optical communication with the second light source, the gas is disposed at least in part between the first and second layers of algae, and light from the second light source travels through the second layer of algae and toward the first surface of the first layer of algae.

In an embodiment:

the one or more photosynthetic oxygen supplies includes first and second oxygen supplies, the first oxygen supply includes the first layer of algae and the first light source, the second oxygen supply includes the second layer of algae and the second light source, light from the first light source is configured to provide light for the first layer of algae and for at least a portion of the second layer of algae, and light from the second light source is configured to provide light for the second layer of algae and at least a portion of the first layer of algae.

In an embodiment, the second layer of algae has a width of between 100 um and 2000 um.

In an embodiment, the second layer of algae has a width of between 100 um and 300 um.

In an embodiment, the one or more photosynthetic oxygen supplies include a plurality of oxygen supplies.

In an embodiment, each of the plurality of oxygen supplies is spaced apart from an adjacent one of the oxygen supplies by an area, a width thereof being between 100 um and 300 um.

In an embodiment, the apparatus includes a channel in communication with the area, the channel configured to collect a portion of the oxygen from the area and to transport the oxygen to the functional cells.

In an embodiment, the gas is disposed at least in part between each photosynthetic oxygen supply.

In an embodiment, each photosynthetic oxygen supply includes:

a light source; and at least one layer of algae, positioned to receive light from the light source.

In an embodiment, the at least one layer of algae is in contact with the gas.

In an embodiment, the at least one layer of algae includes a first and a second layer of algae, and the light source is disposed between the first and second layers of algae.

In an embodiment, both the first and second layers of algae are in contact with the gas.

There is further provided, in accordance with an embodiment of the present invention, apparatus, including:

a housing having at least one outlet;

one or more photosynthetic oxygen supplies disposed within the housing and in communication with the outlet; and a gas disposed to permit passage therethrough of oxygen generated from the one or more oxygen supplies toward the outlet, the gas disposed at least in part between the outlet and at least one of the oxygen supplies.

In an embodiment, each photosynthetic oxygen supply includes:

a light source; and at least one first layer of algae, positioned to receive light from the light source.

In an embodiment, the light source has an input electrical power between 5 mW/(cm^2 of algae) and 50 mW/(cm^2 of algae).

In an embodiment, an energy of illumination applied to the layer of algae is at a rate of between 0.2 mW/(cm^2 of algae) and 2.0 mW/(cm^2 of algae).

In an embodiment, the first layer of algae has a width of between 100 um and 2000 um.

In an embodiment, the first layer of algae has a width of between 100 um and 300 um.

In an embodiment, the light source includes a first light source configured to be in optical communication with at least a first surface of the first layer of algae, and the apparatus further includes a second light source configured to be in optical communication with at least the first surface of the first layer of algae, the first layer of algae being disposed between the first and second light sources.

In an embodiment:

the apparatus includes a second layer of algae, the second layer of algae being in optical communication with the second light source, the gas is disposed at least in part between the first and second layers of algae, and light from the second light source travels through the second layer of algae and toward the first surface of the first layer of algae.

In an embodiment:

the one or more photosynthetic oxygen supplies includes first and second oxygen supplies, the first oxygen supply includes the first layer of algae and the first light source, the second oxygen supply includes the second layer of algae and the second light source, light from the first light source is configured to provide light for the first layer of algae and for at least a portion of the second layer of algae, and light from the second light source is configured to provide light for the second layer of algae and at least a portion of the first layer of algae.

In an embodiment, the second layer of algae has a width of between 100 um and 2000 um.

In an embodiment, the second layer of algae has a width of between 100 um and 300 um.

In an embodiment, the at least one layer of algae is in contact with the gas.

In an embodiment, the gas is disposed in part between the layer of algae and the light source.

In an embodiment, the at least one layer of algae includes a first and a second layer of algae, and the light source is disposed between the first and second layers.

In an embodiment, both the first and second layers of algae are in contact with the gas.

In an embodiment, both the first and second layers of algae are in contact with the light source.

In an embodiment, the one or more photosynthetic oxygen supplies include a plurality of oxygen supplies.

In an embodiment, the gas is disposed at least in part between each photosynthetic oxygen supply.

In an embodiment, the housing is configured for insertion into a body of a subject, and the gas is configured to permit passage therethrough of the oxygen from the photosynthetic oxygen supply toward the outlet and subsequently to a vicinity in the body of the subject that is external to the housing.

In an embodiment, the housing includes a semi-permeable membrane having associated therewith a molecular weight cutoff, the membrane being disposed with respect to the housing so as to protect the photosynthetic oxygen supply from components of a body fluid of the subject having molecular weights higher than the cutoff.

In an embodiment, the membrane includes a gas-permeable membrane.

There is additionally provided, in accordance with an embodiment of the present invention, apparatus, including:

a housing;

at least a first layer of a photosynthetic source disposed within the housing, the layer having at least a first surface;

at least a first light source in optical communication with the first surface of the first layer of the photosynthetic source;

at least a second light source in optical communication with the first surface of the first layer of the photosynthetic source; and a gas disposed to permit passage therethrough of oxygen from the first layer of the photosynthetic source.

In an embodiment, the first surface of the photosynthetic source is in contact with the gas.

In an embodiment, the photosynthetic source is in contact with the first light source.

In an embodiment, the first and second light sources each have an input electrical power between 5 mW/(cm^2 of algae) and 50 mW/(cm^2 of algae).

In an embodiment, an energy of illumination applied to the algae by the first and second light sources is at a rate of between 0.2 mW/(cm^2 of algae) and 2.0 mW/(cm^2 of algae).

In an embodiment, the layer of the photosynthetic source has a width of between 100 um and 2000 um.

In an embodiment, the layer of the photosynthetic source has a width of between 100 um and 300 um.

In an embodiment:

the at least a first layer of the photosynthetic source includes first and second layers of photosynthetic sources, the second layer of the photosynthetic source being in optical communication with the second light source, the gas is disposed at least in part between the first and second layers of the photosynthetic sources, and light from the second light source travels through the second layer and toward the first surface of the first layer.

In an embodiment, the second layer has a width of between 100 um and 2000 um.

In an embodiment, the second layer has a width of between 100 um and 300 um.

In an embodiment, the housing includes at least one layer of functional cells configured to receive oxygen from the photosynthetic source, and the gas is disposed at least in part between the layer of cells and the photosynthetic source and is configured to permit passage therethrough of the oxygen from the photosynthetic source to the cells.

In an embodiment, the functional cells include pancreatic islet cells.

In an embodiment, the photosynthetic source includes algae, and the apparatus further includes a membrane disposed between the photosynthetic source and the functional cells, the membrane having associated therewith a molecular weight cutoff configured to restrict passage of algae therethrough.

In an embodiment, the membrane includes a gas-permeable membrane.

In an embodiment, the housing is configured for insertion into a body of a subject, and the gas is configured to permit passage therethrough of the oxygen from the photosynthetic source toward a vicinity in the body of the subject that is external to the housing.

In an embodiment, the housing includes a semi-permeable membrane having associated therewith a molecular weight cutoff, the membrane being disposed with respect to housing so as to protect the photosynthetic source from components of a body fluid of the subject having molecular weights higher than the cutoff.

In an embodiment, the membrane includes a gas-permeable membrane.

The present invention will be more fully understood from the following detailed description of embodiments thereof, taken together with the drawings, in which:

DETAILED DESCRIPTION OF EMBODIMENTS

Figure 1:
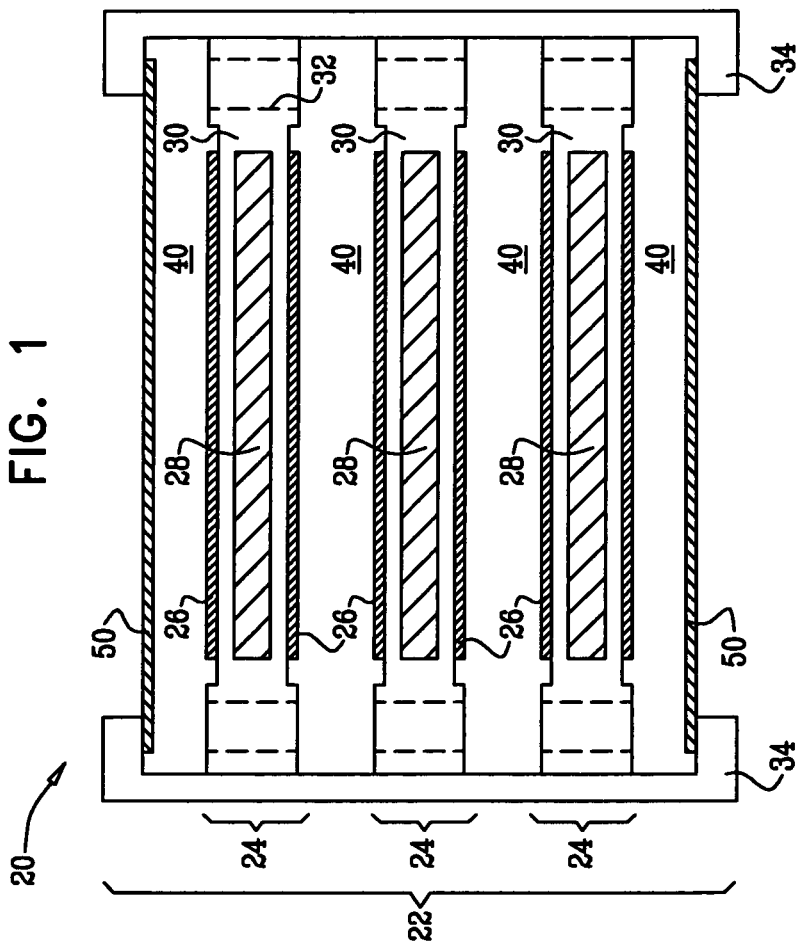
FIG. 1 is a schematic illustration of an oxygen generator, in accordance with an embodiment of the present invention.
Figure 2:
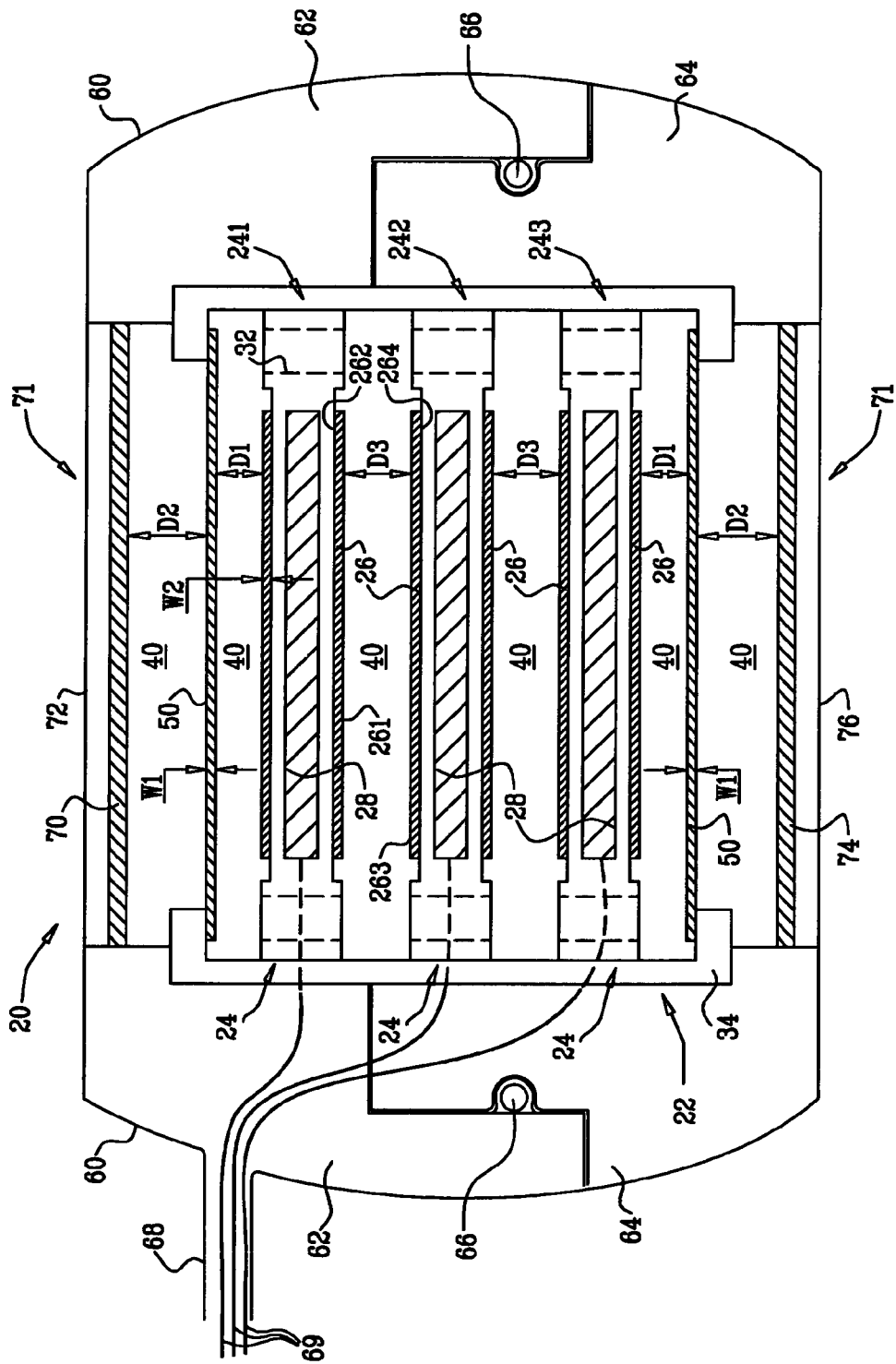
FIG. 2 is a schematic illustration of a housing comprising the oxygen generator of FIG. 1 and layers of functional cells, in accordance with an embodiment of the present invention.

Reference is now made to FIGS. 1 and 2, which are schematic illustrations of a system 20 comprising an oxygen generator 22 configured to generate and supply oxygen to respective first and second layers 70 and 74 of functional cells, in accordance with an embodiment of the present invention. Typically, the functional cells disposed within layers 70 and 74 comprise pancreatic islets of Langerhans cells. Layers 70 and 74 of functional cells comprise a metal grid (not shown) which houses a substrate to which the cells adhere, e.g., a liquid or gel, such as alginate, agarose, or polyethylene glycol (PEG). Alternatively, layers 70 and 74 are shaped to provide a three-dimensional biodegradable or non-biodegradable fibrillar matrix upon which the cells are dispersed.

Oxygen generator 22 and layers 70 and 74 of functional cells are disposed within a housing 60 which is configured for implantation within a body of a subject. Typically, oxygen generator 22 generates sufficient oxygen to sustain the functional cells during the period preceding vascularization of fibrotic tissue that forms around housing 60. The immediate supply of oxygen to the cells enables proper function of the cells immediately following implantation. Typically, oxygen generator 22 generates oxygen in real-time by photosynthesis. For some applications, the oxygen generator continues to provide oxygen to the cells during the period following the vascularization of the fibrotic tissue.

FIG. 1 shows oxygen generator 22 comprising an oxygen supply housing 34 which, in turn, holds at least one photosynthetic oxygen supply 24. Each photosynthetic oxygen supply 24, in turn, comprises a light source 28, e.g., at least one LED coupled to a light-propagating means such as an illuminating panel, and at least one layer 26 of algae disposed around light source 28. As shown, layers 26 of algae are disposed adjacently to light source 28 and at a suitable distance therefrom. In some embodiments, layers 26 contact light source 28 (configuration not shown).

In some embodiments, light source 28 has an input electrical power between 5 mW/(cm$^2$ of algae) and 50 mW/(cm$^2$ of algae). Typically, an energy of illumination applied to layers 26 of the algae is at a rate of between 0.2 mW/(cm$^2$ of algae) and 2.0 mW/(cm$^2$ of algae).

In some embodiments, oxygen generator 22 comprises between one and four (e.g., typically, two) layers of photosynthetic oxygen supplies 24. A respective air gap 40 is disposed in fluid communication with layers 26 of algae of each photosynthetic oxygen supply 24 and between oxygen generator 22 and layers 70 and 74 of functional cells. The layers of photosynthetic oxygen supplies 24 each comprise one or more layers 26 of algae. Typically, layers 26 of algae provide a large surface area in which a ratio of the surface area of the algae to the surface area of layers 70 and 74 of functional cells is greater than 1:1.

Air gaps 40 of system 20 provide a means by which oxygen molecules permeate through a gaseous medium with minimal resistance from an area of high concentration (i.e., layers 26 of algae) to an area of low concentration (i.e., layers 70 and 74 of functional cells).

As shown, each oxygen supply 24 comprises a scaffold 30 which houses light source 28 and the algae. Scaffold 30 comprises a substrate, e.g., agarose or optically-transparent plastic, surrounding light source 28. Typically, a first and a second layer 26 of algae are disposed upon scaffold 30 adjacent to respective first and second surfaces of light source 28. Such disposition of layers 26 with respect to light source 28 increases a surface area of algae exposed to light emitted from source 28, effectively increasing a rate of photosynthesis of the algae.

In some embodiments, light source 28 comprises a plurality of LEDs coupled to a plastic illuminating panel which conducts the light emitted from the LEDs.

Reference is again made to FIGS. 1 and 2. Each photosynthetic oxygen supply 24 is separated from the next oxygen supply 24 by an air gap 40 comprising a gas, e.g., air enhanced by oxygen and carbon dioxide. The gas is disposed in air gap 40 between adjacent oxygen supplies 24 such that each layer 26 of algae is in fluid communication with the gas, and oxygen generated by the algae is diffused into air gap 40. The presence of the gas disposed within air gap 40 is hypothesized by the inventors to increase the diffusivity of the oxygen through air gap 40 and ultimately toward layers 70 and 74 of functional cells. The gas disposed within air gap 40 also enables storage therein of a large amount of gaseous oxygen produced from the algae. As shown in FIG. 2, each air gap 40 between respective oxygen supplies 24 (which, in the context of FIG. 2, are oxygen supplies 241, 242, and 243) is shaped to define a distance D3 of between 100 um and 300 um, e.g., 200 um.

Scaffolds 30 are shaped to provide at least one channel 32 configured for passage therethrough of the oxygen generated by oxygen supplies 24 to layers 70 and 74 of functional cells. As shown in the embodiments of the figures, channels 32 facilitate continuous gas communication among the various air gaps 40. Since the functional cells consume oxygen at a variable rate depending on local conditions (e.g., blood glucose level), and since the algae in layers 26 produce oxygen at a variable rate depending on local conditions (e.g., light intensity levels), air gaps 40 function as oxygen reservoirs storing the generated oxygen until the oxygen is diffused upon need therefor to the functional cells. Such storing regulates a concentration of oxygen within housing 60.

Thus, when light is provided at a constant rate, the algae produce oxygen at a constant rate, all other things being equal. The oxygen is then diffused into air gaps 40 where, depending on the need for oxygen consumption by the functional cells, the oxygen molecules may: (1) diffuse through air gaps 40 and toward the functional cells where it is used immediately, (2) be stored in air gaps 40 until there exists a demand for oxygen by the functional cells, or (3) once air gaps 40 are saturated with oxygen and when the functional cells do not need or consume the available oxygen stored in air gaps 40, permeate through cell layers 70 and 74, through membranes 72 and 76, respectively, and toward surrounding tissue of the subject.

Additionally, a light regulator (not shown) is typically coupled to housing 60, to regulate the concentration of oxygen in housing 60 by regulating the rate of production of oxygen by the algae. The light regulator typically regulates the intensity of light emitted from light source 28 of each oxygen supply 24, or a pulse rate or a duty cycle of the emitted light.

As shown in FIG. 2, each layer 26 of algae is shaped to define a width W2 of between 10 um and 2000 um, typically, between 100 um and 2000 um, e.g., between 100 um and 300 um. Additionally, each layer 26 of algae is disposed substantially in a planar configuration defining dimensions of between about 0.05 cm by 0.05 cm and about 10 cm by 10 cm (e.g., 1.3 cm by 1.8 cm).

FIG. 2 shows oxygen generator 22 comprising oxygen supplies 241, 242, and 243. Width W2 of each layer 26 of algae in each oxygen supply 24: (a) optimizes the propagation of light from light source 28 within layer 26, (b) reduces the relative oxygen concentration disposed within layers 26, and (c) facilitates a proper oxygen flux between layers 26 and air gaps 40. Width W2 of algae layers 26 enables most of the algae to absorb generally around 90% of light emitted from light source 28.

Additionally, width W2 of layer 26 facilitates transmission of light to algae layer 26 of a first oxygen supply 24 from a neighboring light source 28 of a second oxygen supply 24. This is because the small width of algae layer 26 disposed adjacently to light source 28 of the second oxygen supply facilitates transmission of light through layer 26 of algae and toward algae layer 26 of the first oxygen supply. For example, due to a relatively thin width W2 of algae layer 26, sufficient light generated by light source 28 of oxygen supply 241 is able to propagate beyond surface 261 of algae layer 26 of oxygen supply 241, and toward surface 263 of algae layer 26 of oxygen supply 242. Additionally, surface 263 of algae layer 26 of oxygen supply 242 also receives light that is generated by light source 28 of oxygen supply 242 because, due to the relatively thin width W2 of algae layer 26, light is able to propagate through (and beyond) algae layer 26.

Thus, the light intensity, or irradiance, at a given surface of a given algae layer 26 (i.e., the surface that is disposed in optical communication with the light source of a neighboring oxygen supply) is typically a combination of intensities of:

(1) light that is emitted from the adjacently-disposed light source, and (2) light that is emitted from the neighboring light source.

Figure 3:
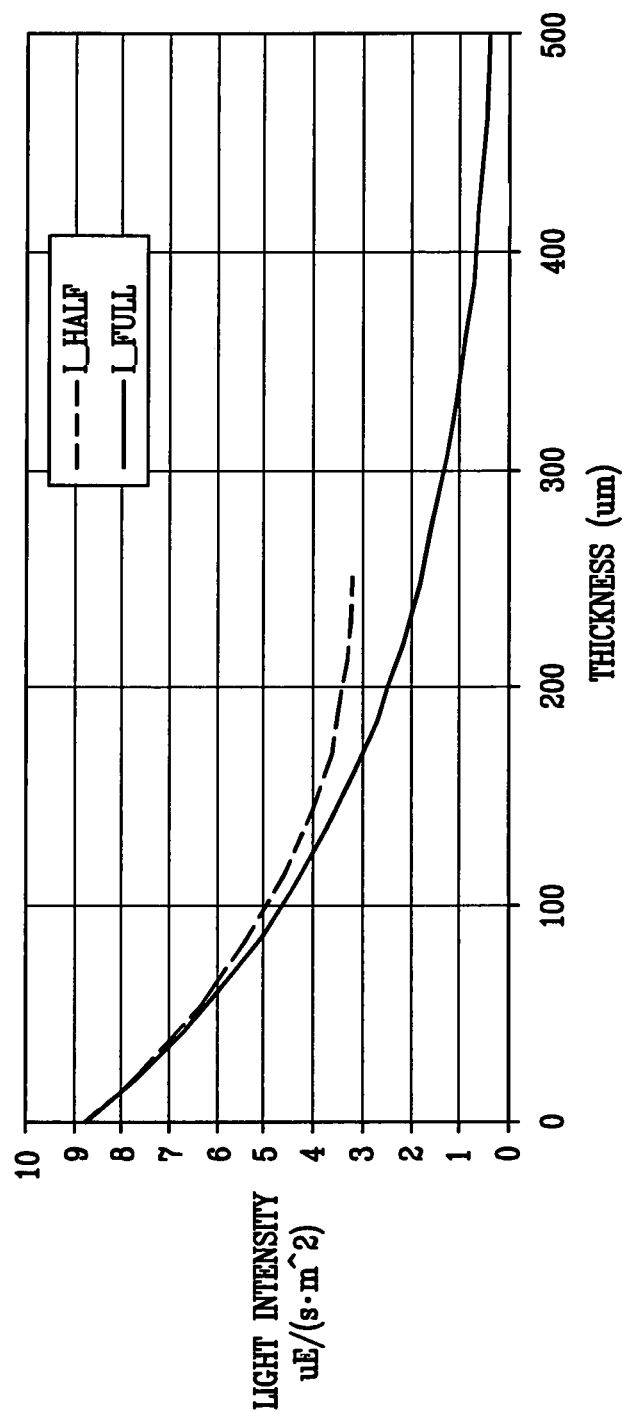
FIGS. 3-5 are graphical representations of calculated, simulated parameters of the oxygen generator, in accordance with an embodiment of the present invention.
Figure 4:
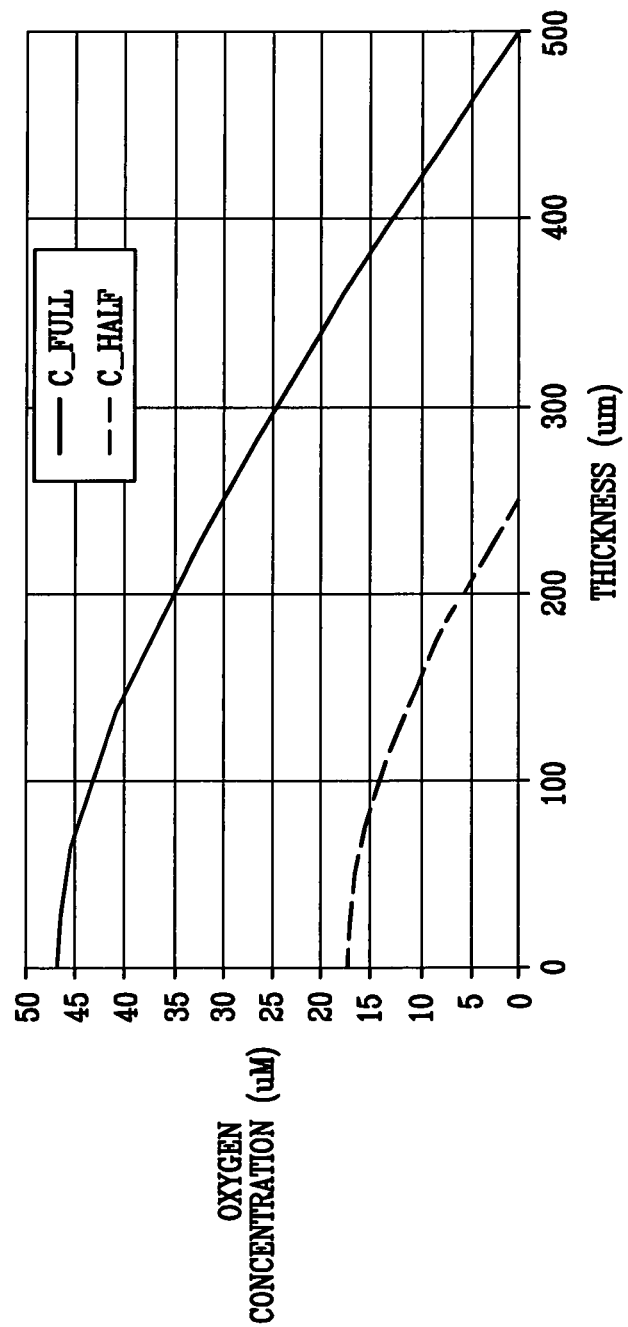
Figure 5:
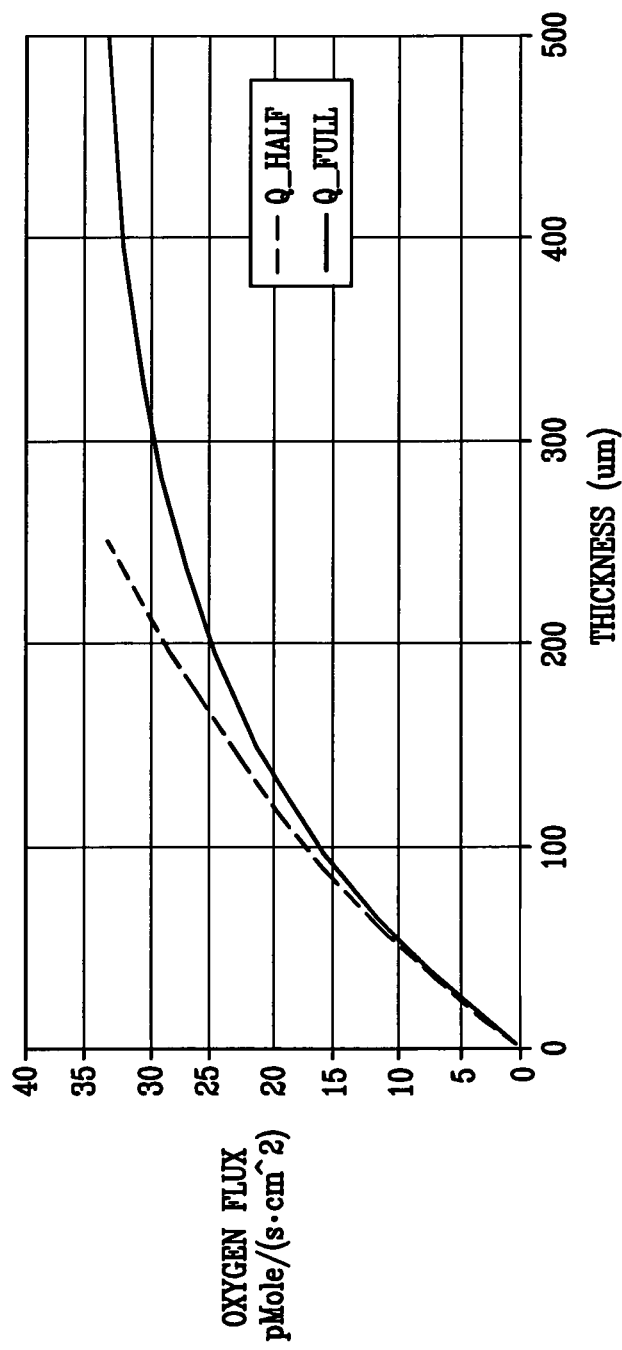

Reference is now made to FIGS. 3-5, which are graphical representations of parameters of the oxygen generator, in accordance with an embodiment of the present invention.

FIG. 3 is a graphical illustration of a comparison of light intensity at various widths (i.e., 250 um and 500 um) of algae layers of respective, adjacently-disposed photosynthetic oxygen supplies. Typically, according to the Beer-Lambert law, light decays exponentially (as shown) through the respective algae layers which have a full width (i.e., 500 um) and have a width that is half the full width (i.e., 250 um). The graph represents the algae layers in which: (a) 0 um defines the surface of the algae layer that is disposed adjacently to the light source, and (b) 250 um or 500 um defines the surface of the respective algae layer that is furthest away from the light source.

Thus, for the algae layer having a width of 500 um, light intensity decays from around 8.8 uE/(s*m^2) at 0 um to around 0.3 uE/(s*m^2) at 500 um, i.e., the algae layer surface furthest from the light source. In contrast, for the algae layer having a width of 250 um, light intensity decays from around 8.8 uE/(s*m^2) at 0 um to around 3:1 uE/(s*m^2) at 250 um, i.e., the algae layer surface furthest from the light source. As described hereinabove with reference to FIG. 2, by reducing the width of the algae layer 26 to around 250 um, light is able to pass through the algae layer of a first oxygen supply and toward the algae layer of a second, neighboring oxygen supply, in order to supplement light to the neighboring layer which also receives light from a light source disposed adjacently thereto. This supplemented light at the surface of the 250 um-wide algae layer increases the light intensity at the surface relative to the light intensity at the surface of a 500 um-wide algae layer.

Although the light intensity has decayed at 250 um from the light source in either curve, the curve representing the 250 um-wide algae layer shows a relatively stronger light intensity at the surface of the 250 um-wide algae layer (i.e., the surface exposed to and in fluid communication with the air gap). This is because, as described hereinabove with respect to FIG. 2, width W2 of layer 26 of algae enables the algae at 250 um from the light source to receive light from the light source disposed adjacently to the algae layer as well as from the light source of a neighboring photosynthetic oxygen supply.

The light intensity at the surface of the 250 um-wide algae layer optimizes the total oxygen production of the entire algae layer since the algae at the surface of the 250 um-wide layer are provided with sufficient light to undergo photosynthesis more efficiently than the algae at the surface of the 500 um-wide algae layer.

FIG. 4 shows relative oxygen concentrations disposed within the 250 um-wide algae layer and within the 500 um-wide algae layer. The graph represents the algae layers in which: (a) 0 um defines the surface of the algae layer that is disposed adjacently to the light source, and (b) 250 um or 500 um defines the surface of the respective algae layer that is furthest away from the light source. Typically, the concentration of oxygen in either algae layer is greatest at 0 um due to the proximity of the algae to the light source.

Figure 6:
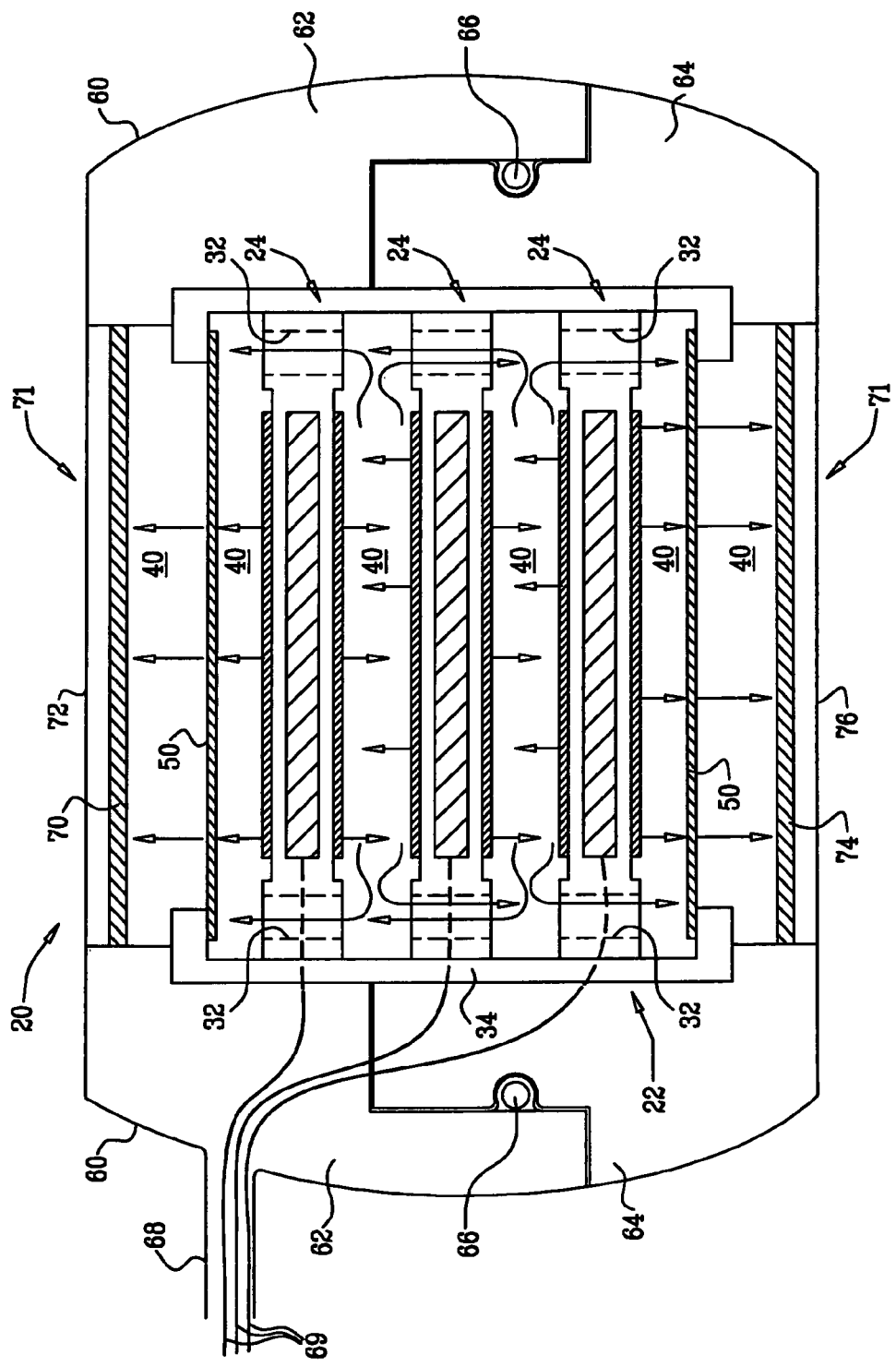
FIG. 6 is a schematic illustration of a flow of oxygen between the oxygen generator and the functional cells, in accordance with an embodiment of the present invention.

Reference is now made to FIGS. 3, 4, and 5, which are graphical representations of calculated, simulated parameters of the oxygen generator, in accordance with an embodiment of the present invention. As described hereinabove with reference to FIG. 3, the algae at the surface of the 250 um-wide layer that is exposed to the air gap receives sufficient light in order to produce oxygen. This oxygen is immediately diffused into the air gap. Additionally, the oxygen produced by the algae layer at 0 um diffuses a relatively shorter distance through the 250 um-wide algae layer than through the 500 um-wide algae layer. Thus, as indicated in FIG. 6, the concentration of oxygen deep in the 250 um-wide algae layer (i.e., ~17 uM) is lower than the concentration of oxygen deep in the 500 um-wide algae layer (i.e., ~48 uM). The 250 um-wide algae layer facilitates enhanced diffusion of oxygen molecules therethrough in order to: (a) reduce the oxygen toxicity of the algae layer (in particular of algae disposed adjacently to light source 28 in surfaces 262 and 264, for example), and (b) diffuse more oxygen molecules into air gap 40.

FIG. 5 shows the oxygen flux for the respective algae layers. As shown, the 250 um-wide and 500 um-wide algae layers both generate substantially equal oxygen fluxes (i.e., 34 pMoles/(s*cm^2)) through their exposed surfaces. Taken together with the information of the graphs with reference to FIGS. 3 and 4, the 250 um-wide algae layer provides an oxygen flux that is substantially equal to the oxygen flux of the 500 um-wide algae layer because: (1) the width of the 250 um-wide algae layer provides a shorter distance for oxygen diffusion toward the air gap, which reduces the oxygen concentration within the algae layer, while (2) the width of the 500 um-wide algae layer provides a longer distance for diffusion of the oxygen through the algae layer which effectively retains the oxygen within the algae layer. Thus, the air gaps in device 20 facilitate oxygen provision to the functional cells while reducing the overall footprint of the device, providing reservoirs for excess oxygen molecules, and facilitating a more effective utilization of the algae in the entire layer.

For embodiments in which oxygen generator 22 of device 20 comprises only one photosynthetic oxygen supply 24, air gaps 40 function provide oxygen reservoirs for excess oxygen molecules and facilitate a more effective utilization of the algae in the entire layer.

For some applications, scaffolds 30 are configured to comprise minerals and/or other substances (e.g., potassium nitrate, sodium chloride, sodium phosphate, and/or a magnesium compound) which regulate a level of humidity within housing 60. Such regulation is effected by controlling the osmotic pressure of water vapor within air gaps 40. Typically, when osmotic pressure is elevated beyond a threshold amount, water vapor condenses. To ensure a level of relative humidity below 100% within housing 60, a concentration of minerals for each scaffold 30 is determined during production of scaffolds 30 such that the minerals will sufficiently absorb the condensed water vapor within air gaps 40 once housing 60 is implanted within the body of the subject. In turn, by reducing the level of humidity within housing 60, the minerals disposed within scaffolds 30 reduce the osmotic pressure in housing 60. The concentration of minerals in scaffolds 30 is chosen such that the minerals will absorb just enough condensed water to: (a) reduce a level of humidity in housing 60, and (b) normalize the osmotic pressure so as to prevent liquid from being absorbed into housing 60 (from a site outside housing 60), should the minerals create a hypo-osmotic environment within housing 60 by absorbing too much water. The appropriate concentration of minerals in scaffolds 30 absorbs condensed water vapor sufficiently such that the algae-growth conditions are not compromised, thereby maintaining a consistent level of moisture within layers 26 of algae.

In some embodiments, in order to prevent drying of the algae, light source 28 is positioned at a distance of 0.1 mm and 2.0 mm away from layers 26 of algae. In such an embodiment, light is generated remotely by light source 28 and is conducted toward the layers of algae via an illuminating panel, via an optically-transparent tube, or via an optical fiber.

In some embodiments, scaffolds 30 comprise a material configured to incrementally secrete the minerals over a period of time. In such an embodiment, the material helps regulate a level of minerals in housing 60 at a given time and helps prevent the algae from being dried out (an effect of an unregulated, continuous presence of a high concentration of minerals). Furthermore, the algae typically consume a portion of the minerals which regulate the osmotic pressure in housing 60. As such, at given intervals, the material which secretes the minerals provides to scaffolds 30 a renewed supply of minerals in the absence thereof. In some embodiments, the secretion of minerals by the material is governed by an open-loop controller which is not responsive to sensed parameters within housing 60. In some embodiments, the secretion of minerals by the material is governed by a closed-loop controller, e.g., a PID controller. In such an embodiment, scaffolds 30 comprise a sensor configured to sense a parameter within housing 60, e.g., osmotic pressure and/or condensation/humidity. The material is then actuated by the controller to secrete the minerals in response to a signal generated by the sensor when the sensor detects an elevated level of humidity and/or osmotic pressure.

Reference is again made to FIG. 2, which is a schematic illustration of a disposition of oxygen generator 22 with respect to housing 60. Housing 60 is typically shaped to provide an upper portion 62 and a lower portion 64 of housing 60. Upper and lower portions 62 and 64 each comprise a respective first and second layer 70 and 74 of functional cells. Prior to implantation of housing 60 in the body of the subject, housing 60 is loaded with oxygen generator 22 such that oxygen generator 22 is disposed between first and second layers 70 and 74 of functional cells. Upper and lower portions 62 and 64 of housing 60 are aligned at least in part to surround oxygen generator 22. An O-ring 66 is disposed within a groove between portions 62 and 64, and then upper and lower portions 62 and 64 are sealed together. O-ring 66 is used as a mechanical pressure seal at an interface between portions 62 and 64. Typically, O-ring 66 functions to maintain the pressure within housing 60 and to prevent leakage of oxygen from within housing 60.

Housing 60 comprises an electrical channel 68 which couples housing 60 to a remote power supply (not shown). Typically, the power supply is implanted within the body of the subject in the vicinity of housing 60. Alternatively, the power supply is disposed outside the body of the subject, e.g., on an article of clothing such as a belt, and channel 68 trandermally couples the power supply to housing 60. Channel 68 houses electrical wires 69, and each electrical wire 69 supplies power to a respective light source 28 of oxygen generator 22.

Oxygen supply housing 34 is shaped to provide at least one gas-permeable membrane 50 configured for diffusion therethrough of the oxygen toward layers 70 and 74 of functional cells. A respective gas-permeable membrane 50 is typically disposed between oxygen generator 22 and layers 70 and 74 of functional cells. Each gas-permeable membrane 50 is typically shaped to define: (a) a width W1 of between 5 um and 1000 um, e.g., between 10 um and 100 um, and (b) a diameter of between 1 cm and 25 cm, e.g., 3.5 cm. Gas-permeable membrane 50 is spaced apart from respective first and second layers 70 and 74 of functional cells by an air gap 40 defining a distance D2. Distance D2 typically ranges from about 1 um to about 1000 um, such as 200-500 um (e.g., 300 um). Gas-permeable membrane 50 is, in turn, spaced apart from a layer 26 of algae by an air gap 40 having a distance of about 0.1 mm to about 6 mm, e.g., 0.5 mm. As described hereinabove, gas is disposed within each air gap 40 between respective layers of housing 60.

Housing 60 typically comprises a selectively-permeable biocompatible membrane 71 encapsulating either the entire housing, or portions thereof (e.g., covering at least layers 70 and 74 of cells, as shown). Membrane 71 comprises an first membrane 72 which is disposed adjacent to layer 70 of cells, and comprises a second membrane 76 which is disposed adjacent to layer 74 of cells. Membrane 71 is typically characterized by a molecular weight cut-off of about 11,000-100,000 daltons, that is adapted to allow passage of nutrients and substances produced or consumed by the cells, such as oxygen, carbon dioxide, glucose, insulin, or water. Membrane 71 of housing 60 also typically immunoisolates the functional cells by preventing passage therethrough of cells of the subject's body, e.g., white blood cells.

Additionally, the gas disposed in each air gap 40 of housing 60 further immunoisolates system 20, since a liquid medium typically facilitates cell motility.

Reference is now made to FIG. 6, which is a schematic illustration of a flow of oxygen within housing 60, in accordance with an embodiment of the present invention. The arrows of FIG. 6 represent the flow of oxygen as it diffuses from oxygen generator 22 toward layers 70 and 74 of functional cells. Since each layer 26 of algae is in contact with air gap 40 comprising the gas, the oxygen molecules generated in layers 26 are diffused into air gap 40. The oxygen can diffuse among and be stored within different air gaps 40 via channels 32 until the oxygen is ultimately diffused through respective gas-permeable membranes 50 toward layers 70 and 74 of functional cells.

It is to be noted that the use of three layers of oxygen supplies 24 is shown by way of illustration and not limitation, and that the scope of the present invention includes embodiments in which between one layer and ten layers, e.g., one layer, of oxygen supplies 24 are used.

Figure 7:
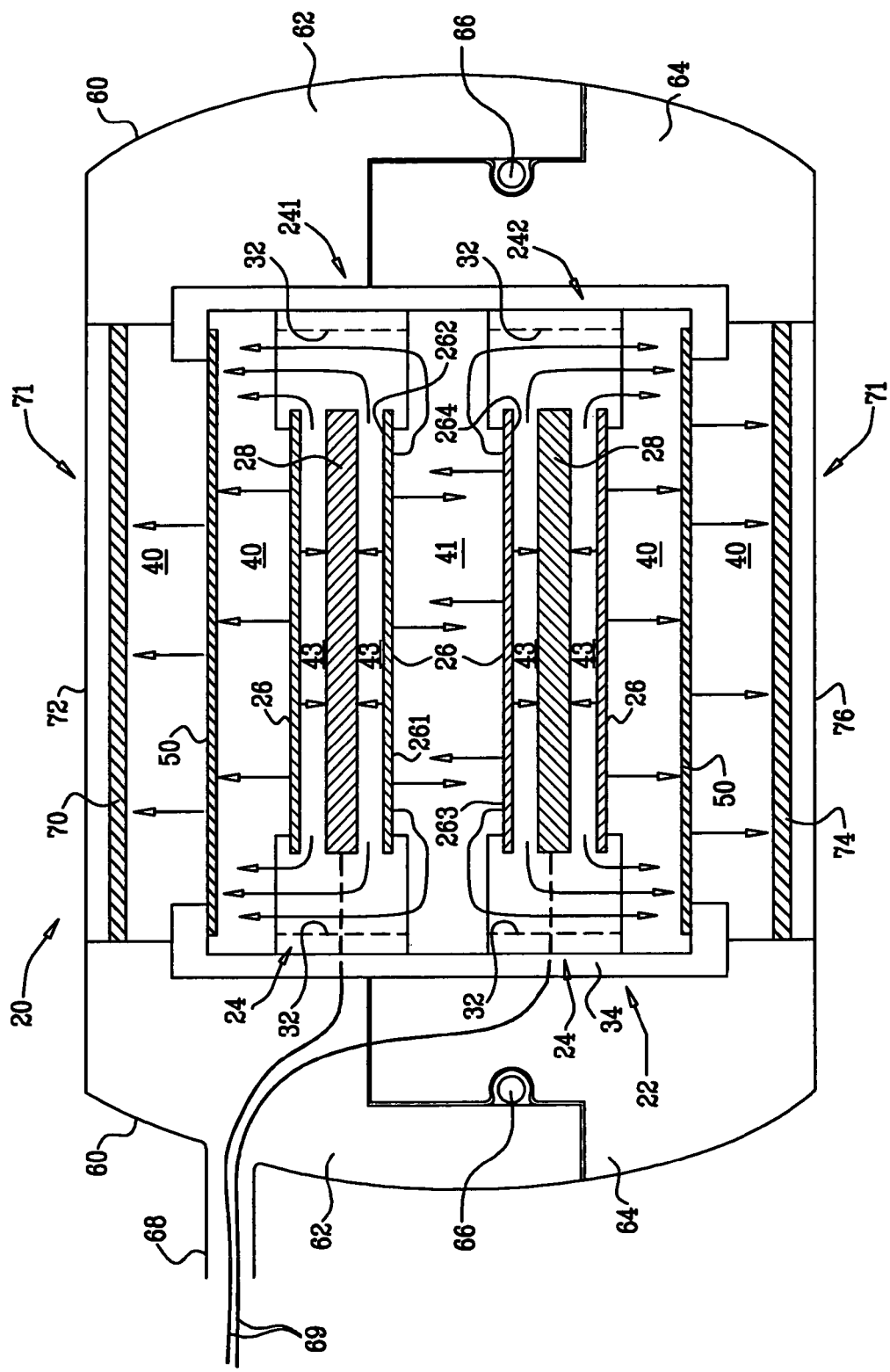
FIG. 7 is a schematic illustration of the housing comprising the oxygen generator, in accordance with another embodiment of the present invention.

Reference is now made to FIG. 7, which is a schematic illustration of system 20 comprising oxygen generator 22 comprising two oxygen supplies 24, which, in the context of FIG. 7, are oxygen supplies 241 and 242, and a plurality of air gaps 43 disposed between layers 26 of algae and light source 28, in accordance with an embodiment of the present invention. Layers 26 of algae comprise algae that are disposed within respective gas-permeable membranes. Support 34 comprises a scaffold that facilitates proper spatial relationship between layers 26 of membrane-bound algae and light source 28.

As shown, for each oxygen supply 24, layers 26 of algae are coupled to support 34 in a manner in which an air gap 43 is disposed between each layer 26 of algae and light source 28. In such an embodiment:

(1) a respective air gap 41 is provided adjacent to each upper surface 261 and 263 of algae layer 26. For example, air gap 41 is in fluid communication with (a) surface 261 of algae layer 26 of supply 241 that is exposed to air gap 41, and (b) surface 263 of layer 26 of algae that of supply 242 that is exposed to the same air gap 41; and (2) a respective air gap 43 is provided between each layer 26 of algae and light source 28. For example, a respective air gap 43 is disposed between each lower surface 262 and 264 of algae layer 26 and light source 28.

Air gaps 41 and 43 allow the oxygen to diffuse from layers 26 and into the housing through both surfaces of layer 26 (i.e., light-remote surfaces 261 and 263 and light-adjacent surfaces 262 and 264 of each layer 26), thereby increasing the diffusion of the oxygen from the algae layer. The algae produce most of the oxygen in the vicinity of the layer that is closest to the light source (i.e., light-adjacent surfaces 262 and 264). The oxygen from the vicinity is allowed to diffuse into air gap 43 via light-adjacent surfaces 262 and 264 without having to diffuse through algae layer 26 first before exiting toward air gap 41 via light-remote surfaces 261 and 263.

It is to be appreciated that the scope of the present invention includes the oxygenation of transplanted cells other than pancreatic islet cells, such as transplanted cells described in references cited in the Background section of the present patent application. For some applications, vascularization around housing 60 is enhanced using one or more biochemical factors (e.g., VEGF) coupled to or in a vicinity of housing 60.

It is to be noted that the scope of the present invention includes the use of device 20 independently of layers 70 and 74 of functional cells. In such an embodiment, device 20 functions as an oxygen generator and comprises an outlet configured for release of the generated oxygen (embodiment not shown). In some embodiments, such a device may be implanted in the body of the subject.

The scope of the present invention includes embodiments described in a US provisional patent application to Rotem et al., entitled, "Protecting algae from body fluids," filed Nov. 22, 2006, which is assigned to the assignee of the present patent application and is incorporated herein by reference. For some applications, techniques described in that provisional patent application are performed in combination with techniques described herein.

For some applications, techniques described herein are practiced in combination with techniques described in one or more of the references cited in the Background section of the present patent application. All references cited herein, including patents, patent applications, and articles, are incorporated herein by reference.

The scope of the present invention includes embodiments described in the following patents and patent applications, which are incorporated herein by reference. In an embodiment, techniques and apparatus described in one or more of the following patents and patent applications are combined with techniques and apparatus described herein:

PCT Patent Publication WO 01/050983, filed Jan. 12, 2001, entitled, "Implantable device";

U.S. patent application Ser. No. 10/466,069, filed Mar. 12, 2004, entitled, "Implantable device" which published as US 2004/0133188, and which issued as U.S. Pat. No. 7,892,222;

US Patent Application Publication 2005/0136092, filed Nov. 30, 2004, entitled, "Implantable device", which issued as U.S. Pat. No. 8,012,500;

PCT Patent Publication WO 06/059322, filed Nov. 27, 2005, entitled, "Implantable device";

U.S. Provisional Patent Application 60/861,592, filed Nov. 28, 2006, entitled, "Oxygen supply for cell transplant and vascularization"; and U.S. Provisional Patent Application 60/860,632, filed Nov. 22, 2006, entitled, "Protecting algae fluids", It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
a housing, configured for insertion into a body of a subject;
one or more oxygen reservoirs disposed within the housing;
at least one layer of functional cells, disposed within the housing; and
gaseous oxygen disposed within the one or more oxygen reservoirs, the apparatus arranged to permit passage of the gaseous oxygen from the one or more oxygen reservoirs to the functional cells,
wherein:
the one or more oxygen reservoirs define first and second air gaps,
the first air gap is configured to receive gaseous oxygen in a first concentration, and
the second air gap is disposed adjacent to the layer of functional cells and stores the gaseous oxygen in a second concentration that is lower than the first concentration.

2. The apparatus according to claim 1, wherein the functional cells comprise pancreatic islet cells.

3. The apparatus according to claim 1, wherein the housing comprises a semi-permeable membrane having associated therewith a molecular weight cutoff, the membrane being disposed with respect to the functional cells so as to protect the functional cells from components of a body fluid of the subject having molecular weights higher than the cutoff.

4. The apparatus according to claim 3, wherein the membrane comprises a gas-permeable membrane.

5. The apparatus according to claim 1, further comprising one or more photosynthetic oxygen supplies disposed within the housing, wherein each photosynthetic oxygen supply comprises:
a light source; and
at least one first layer of algae, positioned to receive light from the light source.

6. The apparatus according to claim 1, wherein the at least one layer of functional cells comprises a first and a second layer of functional cells, and wherein the first and second layers of functional cells are in communication with the gaseous oxygen.

7. The apparatus according to claim 1, wherein the housing further comprises a channel in communication with the one or more oxygen reservoirs, the channel configured to collect a portion of the gaseous oxygen from the one or more oxygen reservoirs and to transport the gaseous oxygen to the functional cells.

8. The apparatus according to claim 1, wherein the apparatus is configured to permit passage of the gaseous oxygen between the one or more oxygen reservoirs and a vicinity in the body of the subject that is external to the housing.

9. The apparatus according to claim 6, wherein the second air gap defines an upper second air gap and a lower second air gap, wherein the upper second air gap is disposed between the first air gap and the first layer of functional cells, and wherein the lower second air gap is disposed between the first air gap the second layer of functional cells.

* * * * *